(12) United States Patent
Okahira et al.

(10) Patent No.: US 6,707,546 B2
(45) Date of Patent: Mar. 16, 2004

(54) APPARATUS FOR INSPECTING A SUBSTRATE

(75) Inventors: Hiroyuki Okahira, Ina (JP); Yuzo Nakamura, Ina (JP); Terumasa Morita, Hachioji (JP); Nobuo Fujisaki, Ina (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 10/042,032

(22) Filed: Oct. 25, 2001

(65) Prior Publication Data

US 2002/0057429 A1 May 16, 2002

Related U.S. Application Data

(62) Division of application No. 09/158,362, filed on Sep. 22, 1998, now Pat. No. 6,362,884.

(30) Foreign Application Priority Data

Sep. 24, 1997 (JP) .............................................. 9-258552
Sep. 18, 1998 (JP) ............................................ 10-264342

(51) Int. Cl.⁷ .............................................. G01N 21/88
(52) U.S. Cl. .................................................. 356/239.1
(58) Field of Search .......................... 356/237.1–237.6, 356/244–246, 239.1–239.8, 600–613, 237, 394, 400–401, 399; 359/379–383, 368

(56) References Cited

U.S. PATENT DOCUMENTS

| | | | | |
|---|---|---|---|---|
| 4,836,667 A | * | 6/1989 | Ozeki | 359/389 |
| 5,171,963 A | * | 12/1992 | Saruta et al. | 219/121.69 |
| 5,479,252 A | * | 12/1995 | Worster et al. | 250/559.42 |
| 5,774,222 A | | 6/1998 | Maeda et al. | |
| 5,787,760 A | | 8/1998 | Thorlakson | |
| 5,923,409 A | | 7/1999 | Hamada et al. | |
| 5,960,106 A | | 9/1999 | Tsuchiya et al. | |

FOREIGN PATENT DOCUMENTS

| | | | |
|---|---|---|---|
| JP | 04-095913 | * | 3/1992 |
| JP | 04-151547 | | 5/1992 |
| JP | 05-109849 | | 4/1993 |
| JP | 05-223521 | | 8/1993 |
| JP | 05-322783 | | 12/1993 |
| JP | 09-243927 | | 9/1997 |

* cited by examiner

*Primary Examiner*—Tu T. Nguyen
(74) *Attorney, Agent, or Firm*—Frishauf, Holtz, Goodman & Chick, P.C.

(57) ABSTRACT

An apparatus for inspecting a substrate includes a substrate holding member for holding a substrate to be inspected, a driving mechanism for raising the substrate holding member to a predetermined angle or less, a position coordinate detecting section provided at side edge of the substrate in at least two directions for detecting coordinates of a defect present in the substrate, an observation system supporting section provided for supporting a micro observation system and moving on the surface of the substrate, and a controlling section for controlling of the movement of the micro observation system of the observation system supporting section to correspond to a defect present in the substrate, on the basis of the position coordinates of the defect detected by the position coordinate detecting section.

9 Claims, 10 Drawing Sheets

APPARATUS FOR INSPECTING A SUBSTRATE

This is a Division of application Ser. No. 09/158,362 filed Sep. 22, 1998, now U.S. Pat. No. 6,362,884.

BACKGROUND OF THE INVENTION

The present invention relates to an apparatus for inspecting defects in a substrate such as a glass substrate for a liquid crystal display (LCD).

Of conventionally-known apparatuses for inspecting defects of LCD glass substrates, some apparatuses are known in which defects (e.g., scratches) formed in the surface of the glass substrate can be checked by using a macro observation and a micro observation interchangeably. In the macro observation, light is applied onto the surface of the glass substrate and then optical change of the reflected glass is observed, thereby detecting the defects. In the micro observation, the defects found by the macro observation are magnified and observed.

For example, Jpn. Pat. Appln. KOKAI No. 5-322783 employs the macro observation system and the micro observation system which are set so as to correspond to an X-Y stage designed movable horizontally in X and Y directions. In the apparatus, the macro observation or the micro observation is performed by mounting a substrate on the X-Y stage and bringing a portion of the substrate to be inspected (defect) into an observation field of the macro observation system or the micro observation system by moving the X-Y stage two-dimensionally in the X and Y directions.

Recently, the size of the glass substrate has tended to be increased with an enlargement of LCDs. In the case where such a large glass substrate is inspected by using the inspecting apparatus having the X-Y stage which is movable horizontally and two-dimensionally (X, Y directions), an area four times as large as the area of the glass substrate is required as a space for moving the X-Y stage. Therefore, the substrate inspecting apparatus has inevitably become large with the increase in size or the glass substrate.

Furthermore, in the conventional inspection apparatus, it is difficult to inspect a small scratch since the surface of the substrate is far away from an eye position of the inspector. Moreover, it is difficult to obtain positional data of the defect found in the surface of the substrate. Accordingly, it is been impossible to inspect the substrate highly accurately.

BRIEF SUMMARY OF THE INVENTION

An object of the present invention is to provide an substrate inspecting apparatus capable of detecting a defect of the substrate efficiently with high accuracy as well as to provide the apparatus in a reduced size.

The substrate inspecting apparatus of the present invention comprises substrate holding member for holding a substrate to be inspected, a driving mechanism for raising the substrate holding member to a predetermined angle or less, a position coordinate detecting section provided at side edge of the substrate in at least two directions, for detecting coordinates of a defect present in the substrate, an observation system supporting section provided for supporting a micro observation system and moving on the surface of the substrate, and a controlling section for controlling of the movement of the micro observation system of the observation system supporting section to correspond to a defect formed present in the substrate, on the basis of the position coordinates of the defect detected by the position coordinate detecting section.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments give below, serve to explain the principles of the invention.

DETAILED DESCRIPTION OF THE INVENTION

Figure 1:
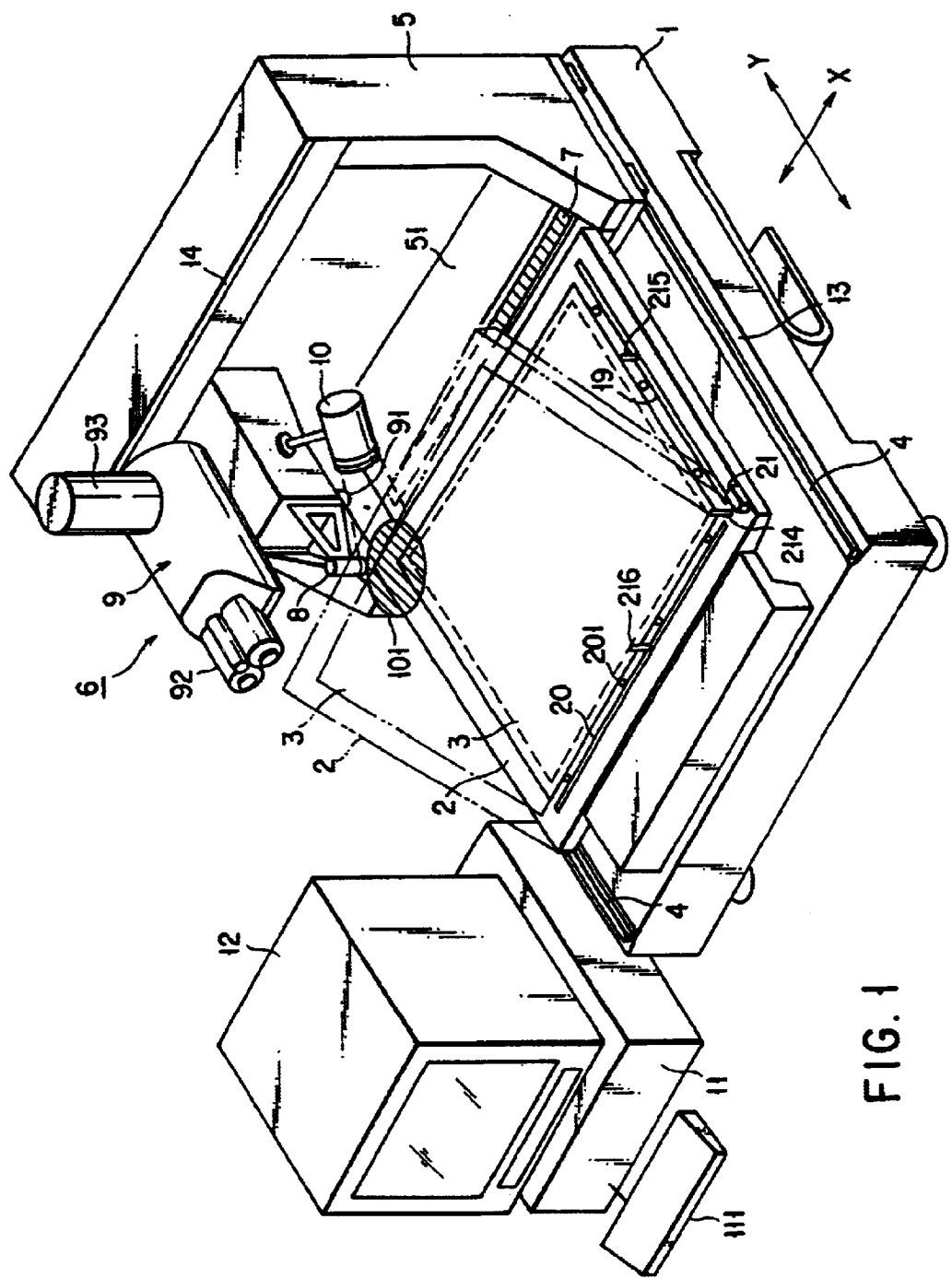
FIG. 1 is a perspective view showing a structure of a substrate inspecting apparatus according to an embodiment of the present invention.
Figure 2:
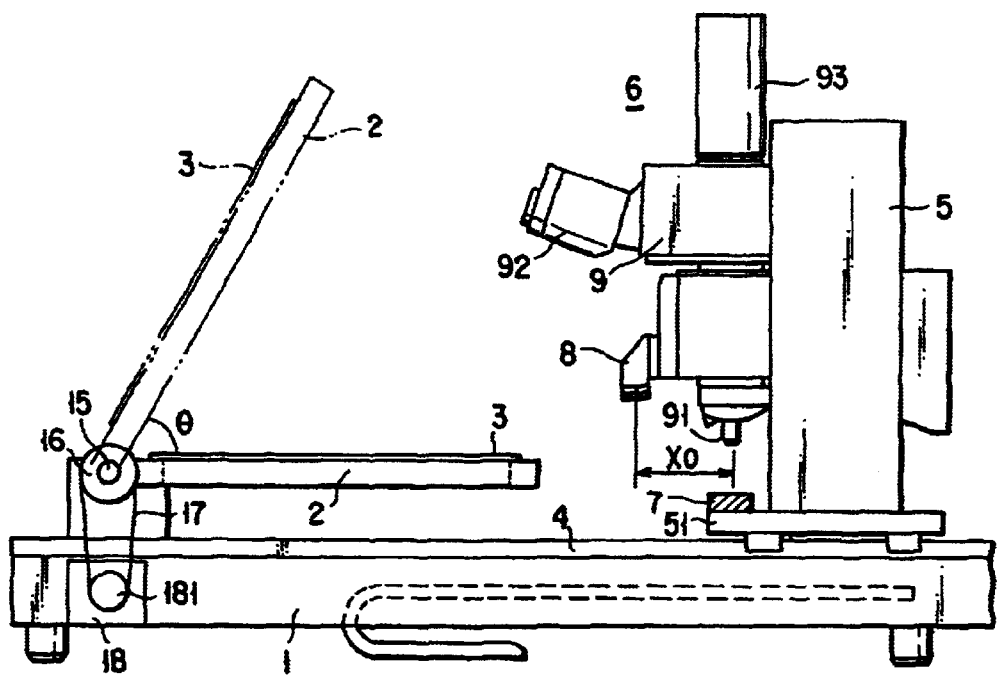
FIG. 2 is a side view showing a structure of the substrate inspecting apparatus according to the embodiment of the present invention.
Figure 3:
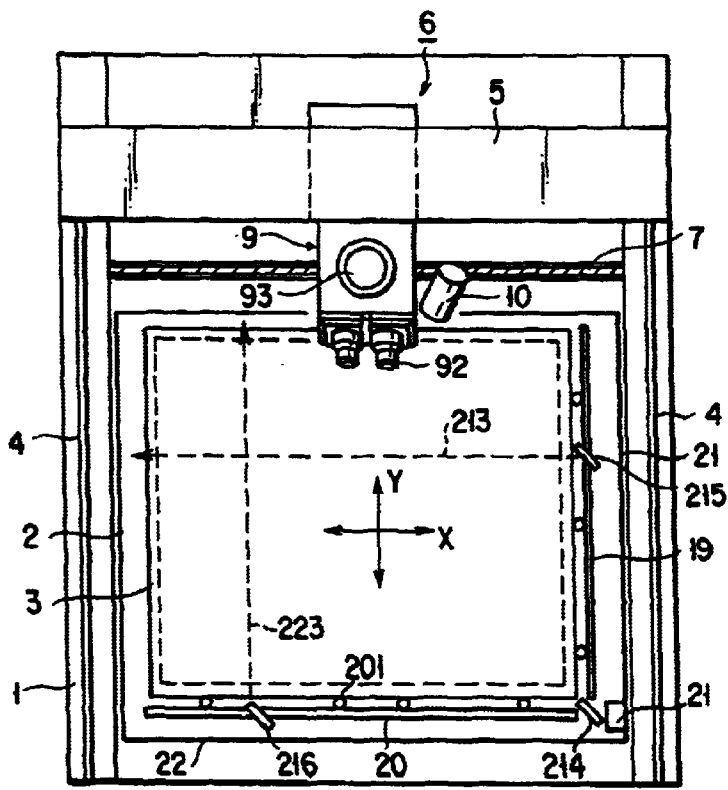
FIG. 3 is a top plan view showing a structure of the substrate inspecting apparatus according to the embodiment of the present invention.

FIGS. 1 to 3 are views showing a structure of the substrate inspecting apparatus according to Embodiment 1 of the present invention. FIGS. 1, 2 and 3 show its perspective view, side view, and top plan view, respectively. In FIGS. 1 to 3, a holder 2 for holding a substrate 3 is provided on the main apparatus 1. As shown in FIG. 2, the holder 2 whose basal portion is supported by a supporting shaft 15 rotatably to the main apparatus 1. A pulley 16 is set in the periphery of the supporting shaft 15. The main apparatus 1 has a motor 18. A ring-form belt 17 is stretched between a rotation shaft 181 of the motor 18 and the pulley 16. When rotational driving force generated by the motor is transmitted from the rotation shaft 181 to the pulley 16 by way of the belt 17, the holder 2 can be raised from a horizontal posture up to a position indicated by two-dot and dashed line, in a rotating manner around the supporting shaft 15. In other words, the holder 2 is raised up to a predetermined angle θ and allowed to stand in an inclined posture.

The holder 2 takes a frame form and mounts the large substrate 3 (e.g., a glass substrate for an LCD) thereon and holds it by the peripheral portion. The holder 2 has a square-form hollow portion surrounded by the peripheral portion and its area is slightly smaller than the substrate 3. The holder 2 has a plurality of substrate urging members 201 (formed of cylindrical pins) along the peripheral portions in the X-axis and Y-axis directions. The urging members 201 are arranged so as to protrude slightly from the surface of the holder 2. The substrate 3 is positioned at a right place on the holder 2 by bringing two sides of the substrate 3 into contact with a side portion of each of the substrate urging members 201. The peripheral portion of the substrate 3 is adsorbed onto the surface of the holder 2 by use of an aspirator (not shown) through a plurality of holes (adsorptive pads) (not shown), which are formed along the entire peripheral portion of the holder 2. By virtue of this mechanism, the substrate 3 is held on the holder 2 without falling out.

Furthermore, guide scales 19, 20 are arranged on the holder 2 along sides of the substrate 3 in the X-axis and Y-axis directions. The guide scales 19, 20 are responsible for detecting coordinates of the defect present in the substrate 3. The guide scale 19 has a reflector (mirror) 215 of the Y-axis direction. The guide scale 20 has a reflector (mirror) 216 of the X-axis direction. The reflectors 215, 216 are provided movably along the guide scales 19, 20, respectively. A beam splitter 214 is fixed on the holder 2 at a point of intersection of extension lines of the guide scales 19, 20. A light source section 21 (described later) is disposed on a position slightly separate from the guide scale 20 (extension line of the guide scale 20) with respect to the beam splitter 214.

As shown in FIGS. 1 to 3, a pair of guide rails 4, 4 are arranged in parallel to the Y-axis direction along both sides of the holder 2 on the main apparatus 1. An observation unit supporting section 5 is arranged above the holder 2 so as to cross over the holder 2. The observation unit supporting section 5 is formed movably along the guide rails 4, 4 in the Y-axis direction above the substrate 3, or above the holder 2.

The observation unit supporting section 5 has an observation unit 6 which is supported movably along a guide rail (not shown) in the X-axis direction perpendicular to the moving direction (Y-axis) of the observation unit supporting section 5. Furthermore, the observation unit supporting section 5 is equipped with a linear transmission light source 7 so as to face a moving line of the observation unit 6. The linear transmission light source 7 is arranged along the X-axis direction on a rear board 51 of the supporting section 5, which moves under the holder 2. Accordingly, the substrate 3 is illuminated by transmission light linearly from the bottom. The linear transmission light source 7 is designed movable in the Y axis direction together with the observation unit supporting section 5.

The observation unit 6 has a micro observation unit 9 equipped with a reference light 8 for use in the micro observation and a partial illumination macro light 10 for use in macro observation. The reference light source 8, which plays a role in identifying defect positions on the substrate 3, projects an optically-converged spot-light upon the surface of the substrate 3. The reflected spot light from the surface of the substrate 3 is brighter than the light emitted from the partial illumination macro light 10 and reflected at the surface of the substrate 3. It is therefore possible to visually perform an observation even if the macro observation process is performed using the partial illumination macro light 10.

The micro observation unit 9 has a microscopic function including an objective lens 91, an ocular lens 92 and an incident light source (not shown). Therefore, an image of the surface of the substrate 3 can be observed through the ocular lens 92 via the objective lens. The micro observation unit 9 is equipped with a TV camera 93 through a tri-lens barrel. When the visual micro observation is not required, a TV camera 93 alone may be set on a liner cylinder. The image of the substrate surface obtained through the objective lens 91 is photographed by the TV camera 93 and sent to a controller 11. The controller 11 instructed to display the photographed image on the TV monitor 12. To the controller 11, an input section 111 is connected so as to enable an inspector to input data and to instruct operations.

The partial illumination macro light 10 is used for the macro observation. The surface of the substrate 3 on the holder 2 is partially illuminated with the macro light 101. The incident angle of the partial illumination macro light source 10 with the substrate surface can be controlled at the most suitable angle for the macro observation.

Figure 4:
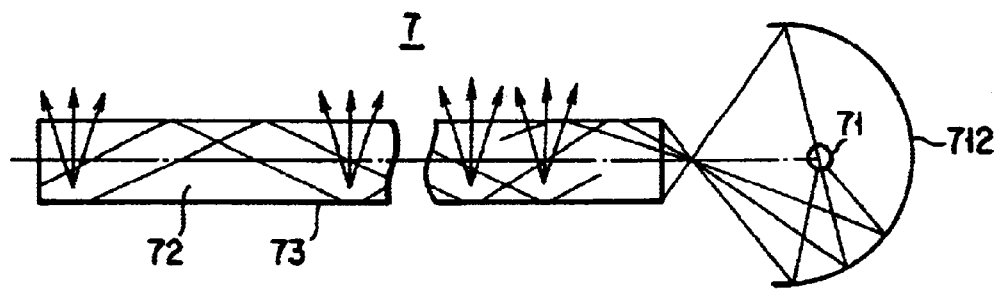
FIG. 4 is a view showing a structure of a transmission linear light according to an embodiment of the present invention.

FIG. 4 is a view showing a structure of the linear transmission light 7. As shown in FIG. 4, the linear transmission light 7 has a light source section 71 and a solid glass rod 72. The light emitted from the light source section 71 is diffusely reflected by the reflecting board 712 and injected into an end of the glass rod 72. The incident light is transmitted through the glass rod 72 while totally reflected and simultaneously dispersed by white stripes 73 (which have been coated and processed into stripes) on a rear portion (lower portion) of the glass rod 72. As a result, linear light is emitted upwardly by virtue of a lens-like function of the glass rod 72. The structure of the linear transmission light is not limited to the aforementioned one. For example, a fluorescent lamp may be employed as the linear illumination.

Figure 5:
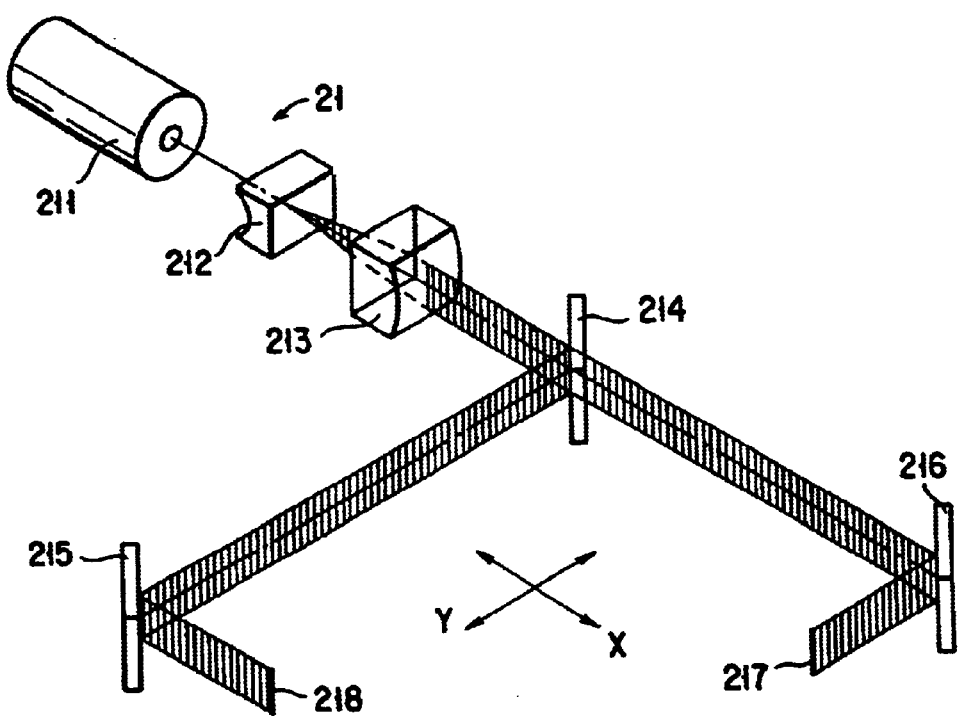
FIG. 5 is a view showing a structure of a position detector according to an embodiment of the present invention.

FIG. 5 is a view showing a structure of a position detector of the substrate inspecting apparatus of the present invention. In FIG. 5, like reference numerals are used to designate like structural elements corresponding to those in FIG. 3. The position detector has a light source section 21, a beam splitter 214 and reflectors (mirrors) 215, 216. The light source section 21 is formed of a laser light source 211 and cylindrical lenses 212, 213. The beams splitter 214 splits the laser light emitted from the laser light source 211 into light beams in the X-axis and Y-axis directions. The reflectors 215, 216 are respectively formed on the guide scales 19, 20. The beam splitter 214 and the reflectors 215, 216 are vertically set at a right angle or an acute angle with the substrate surface 3.

The laser light emitted from the laser light source 211 is transmitted through the cylindrical lenses 212, 213 and finally emitted in the X-axis direction in the form of a planar light virtually perpendicular to the surface of the substrate 3. The planar laser light is split into two beams in the X-axis and Y-axis directions. The laser light beam in the X-axis direction is reflected by the reflector 216 and proceeds in the perpendicular direction, namely, the Y-axis direction, in the form of a planar laser light 217 virtually perpendicular to the surface of the substrate 3. On the other hand, the laser light beam in the Y-axis direction is reflected by the reflector 215 and proceeds in the perpendicular direction, namely, the X-axis direction, in the form of a planer laser light 218 virtually perpendicular to the surface of the substrate 3.

The inspector moves the reflector 215 along the guide scale 19 to permit the laser light 218 to correspond with the defect present in the substrate surface. In the same manner, the inspector moves the reflector 216 along the guide scale 20, thereby permitting the laser light 217 to correspond with the defect. Thereafter, when the inspector turns on a switch (not shown), values of the guide scales 19, 20, that is, moving amounts of the reflectors 215, 216 in the X-axis direction and Y-axis direction from their origins can be detected by respective detectors (not shown) of the guide scales 19, 20, as coordinates (X, Y) of the defect. The detected results are output from the detector to the controller 11. Note that the origin of the coordinate of the reflector 215 is present at the forefront side of the guide scale 19. The origin of the coordinate of the reflector 216 is present at the rightmost end of the guide scale 20 (see FIG. 3).

Figure 6:
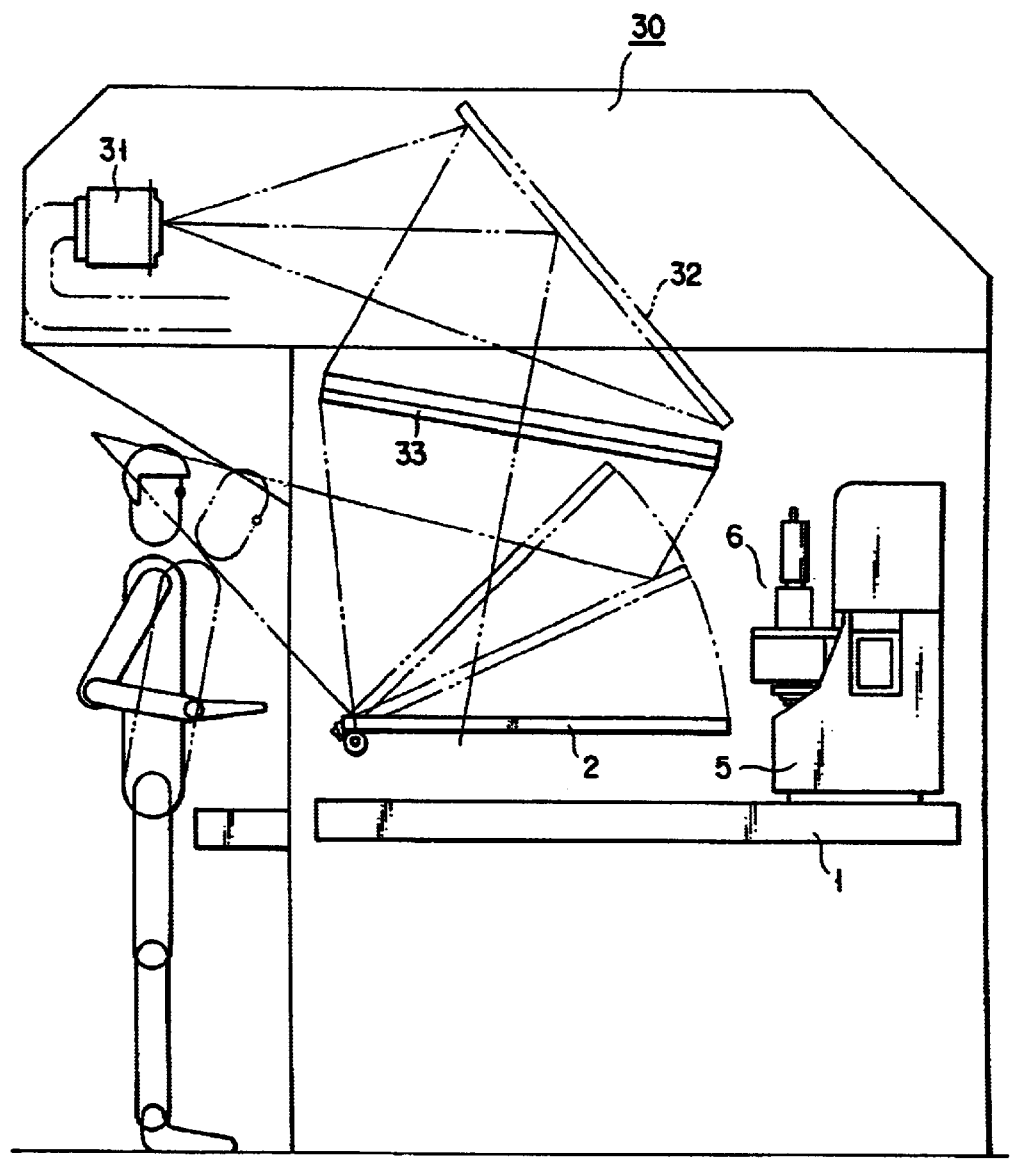
FIG. 6 is a view showing how to inspect a substrate, according to an embodiment of the present invention.

FIG. 6 shows how to inspect a substrate by use of the inspecting apparatus of the present invention. As shown in FIG. 6, an entire-area illuminating macro light source 30 is set above the main apparatus 1. The macro light source irradiates the entire area of the surface of the substrate 3 on the holder 2. The macro light source 30 comprises a metal halide lamp 31 serving as a point light source, a reflecting mirror 32 arranged so as to face the metal halide lamp 31, and a fresnel lens 33 arranged below the reflecting mirror 32. The reflecting mirror 32 is tilted at an angle of 45° with the main apparatus 1 and plays a role in reflecting light incident from the metal halide lamp 31 and injected into the fresnel lens 33. The fresnel lens 33 converges the light reflected by the reflecting mirror 32, as shown in the figure, and injects the converged light over the entire surface of the substrate 3 on the holder 2. Note that, as shown in FIG. 1, the main apparatus 1 has a Y-scale 13 for detecting the position coordinate of the observation unit supporting section 5 in the Y-axis direction. An X-scale 14 is provided on the observation unit supporting section 5 for detecting the position coordinate of the observation unit 6 in the X-axis direction.

The controller 11 shown in FIG. 1 is responsible for not only position coordinates (X, Y) of the defect detected by the guide scales 19, 20 and position coordinates of the observation unit supporting section 5 and the observation unit 6 detected by the Y-scale 13 and the X-scale 14, but also movement control of the observation unit supporting section 5 and the observation unit 6 by a driving mechanism (not shown). Furthermore, the controller 11 has a memory (not shown) for storing data of the interval X0 between an optical axis of the reference light source 8 and an optical axis of the objective lens 91. The control 11 controls movements of the observation unit supporting section 5 and the observation unit 6 so as to permit the optical observation axis of the objective lens 91 of the micro observation unit 9 to correspond with the position coordinates (X, Y) of the defect in the substrate 3 given by the guide scales 19, 20.

While a spot of the reference light 8 is being focused on the defect present in the substrate 3, the controller 11 controls the movements of the observation unit supporting section 5 and the observation unit 6 upon receiving a predetermined instruction given by the inspector from the input section 111. To explain more specifically, first, the position coordinates of the defect are obtained from the position coordinate data of the X-scale 13 and Y-scale 13, detected by detectors (not shown) of the Y scale 13 and the X-scale 14. Then, on the basis of the coordinate data thus obtained and the data of the interval X0 between the optical axis of the reference light 8 and the optical axis of the objective lens 91, the observation unit supporting section 5 and the observation unit 6 are moved in such a way that the observation axis of the objective lens 91 corresponds to the defect present in the substrate 3.

Now, how to operate the substrate inspecting apparatus thus constructed will be explained. In the case of the macro observation of the surface of the substrate 3, the operation is performed as follows. First, the inspector gives a predetermined instruction from the input section 111 to the controller 11. Then, the controller 11 instructs the observation unit supporting section 5 to move backward to the initial position shown in FIG. 1. Thereafter, the inspector places the substrate 3 onto the holder 2 placed horizontally. Upon setting of the substrate 3 at a right position on the holder 2 by a plurality of substrate urging members 201, the substrate 3 is adsorbed onto the holder 2 by the aspirator so as not to drop from the holder 2. In this way, the macro inspecting observation of the defect is initiated.

Next, we will explain how to perform the macro observation of the entire surface of the substrate 3 using the macro light, at one time. First, the motor 18 shown in FIG. 2 is driven by the inspector, thereby rotating the supporting shaft 15 through the pulley 16 via the rotation shaft 181 and the belt 17. The holder 2 is then tilted at a predetermined angle θ, preferably FIG. 6 shows how to inspect a substrate by use of the inspecting apparatus of the present invention. As shown in FIG. 6, an entire-area illuminating macro light source 30 is set above the main apparatus 1. The macro light source irradiates the entire area of the surface of the substrate 3 on the holder 2. The macro light source 30 comprises a metal halide lamp 31 serving as a point light source, a reflecting mirror 32 arranged so as to face the metal halide lamp 31, and a fresnel lens 33 arranged below the reflecting mirror 32. The reflecting mirror 32 is tilted at an angle of 45° with the main apparatus 1 and plays a role in reflecting light incident from the metal halide lamp 31 and injected into the fresnel lens 33. The fresnel lens 33 converges the light reflected by the reflecting mirror 32, as shown in the figure, and injects the converged light over the entire surface of the substrate 3 on the holder 2. Note that, as shown in FIG. 1, the main apparatus 1 has a Y-scale 13 for detecting the position coordinate of the observation unit supporting section 5 in the Y-axis direction. An X-scale 14 is provided on the observation unit supporting section 5 for detecting the position coordinate of the observation unit 6 in the X-axis direction. 30–45° around the supporting shaft 15. Thereafter, the motor is stopped to terminate the movement of the holder 2. Subsequently, a metal halide lamp 31 shown in FIG. 6 is lighted on by the inspector. The light from the metal halide lamp 31 is converged by the reflection mirror 32 and the fresnel lens 33, and then applied onto the entire surface of the substrate 3 on the holder 2. While maintaining this state, the substrate 3 on the holder 2 is visually inspected by the naked eye of the inspector for scratches. Note that the defect is inspected while not only staying the holder 2 at a predetermined angle but also swinging the holder 2 at a predetermined angular range around the supporting shaft 15 by changing a rotation direction of the motor 18 periodically under control of the controller 11. In the later case, it is possible to change the angle of the light supplied from the metal halide lamp 31 incident onto the substrate 3, so that the substrate 3 can be inspected under the illumination light incident from various angles.

Figure 7:
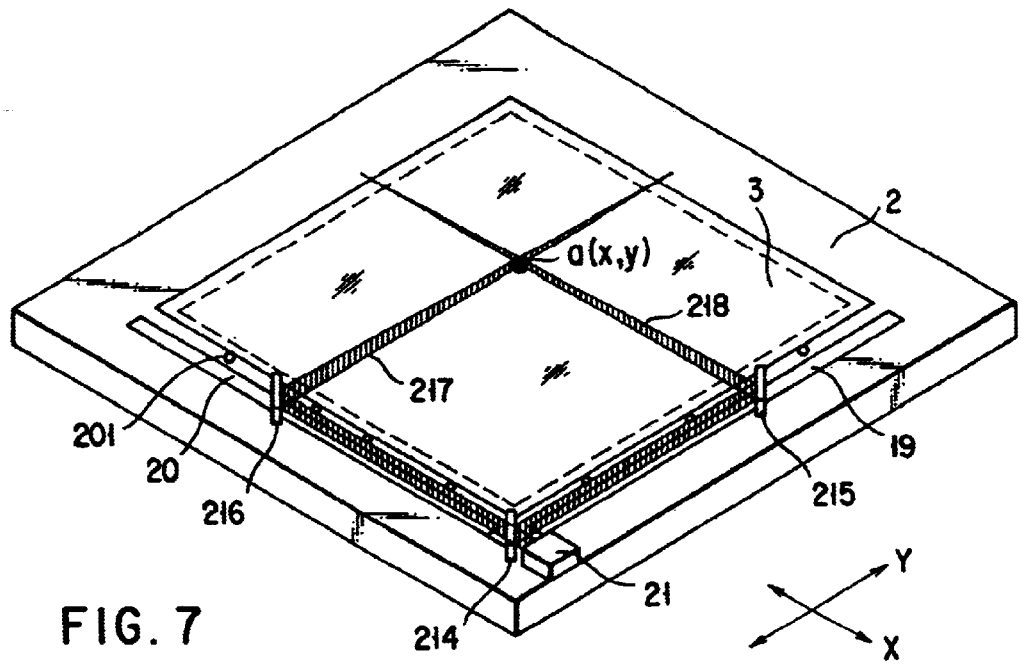
FIG. 7 is a view showing a holder according to an embodiment of the present invention.

FIG. 7 is a view showing the holder 2 having the substrate 3 with a defect. When the inspector recognizes a defect a in the substrate 3 during the macro observation, as show n in FIG. 7, the inspector moves the reflector 215 along the guide scale 19 so as to permit the laser light 218 to correspond with the defect a. Subsequently, the inspector moves the position reflector 216 along the guide scale 20 to permit the laser light 217 to correspond with the defect a. At this point, the position coordinates (X, Y) of the defect a are determined by reading the scale values of the guide scales 19, 20 at which the reflectors 215, 216 are located by the detectors of the guide scales 19, 20. The detected results are output from the detector into the controller 11. In this way, the data showing the position coordinates (X, Y) of the defect a is stored in the memory of the controller 11. Thereafter, the same operation is repeated whenever the inspector recognizes a defect in the substrate 3 and the data indicating the position coordinates (X, Y) of each defect is stored in the controller 11. After the macro observation over the entire surface of the substrate 3 is completed, the motor 18 is driven again by the inspector to rotate the supporting shaft 15 in the opposite direction as mentioned above, through the pulley 16 via the rotation shaft 181 and the belt 17. In this way, the holder 2 is returned to a horizontal posture initially taken.

Next, we will explain how to perform the micro observation of each defect which has been found by the macro observation by use of the micro observation unit 9. First, the position coordinates (X, Y) of the defect stored in the memory are read out by the controller 11. Then, the observation unit supporting section 5 and the observation unit 6 are moved along the guide rails 4, 4, and a guide rail (not shown) in such a manner that the observation axis of the objective lens 91 in the micro observation unit 9 corresponds to the coordinates under the control of the controller 11.

With this operation, the defect present in the substrate 3, i.e., an image of the defect obtained through the objective lens 91 can be microscopically observed by looking into the ocular lens 92 of the micro observation unit 9. In the case where the image of the defect found in the surface of the substrate 3 is photographed by the TV camera 93 and displayed on the TV monitor 12, the micro observation of the defect is performed by watching the image on the TV display.

Next, we will explain the case in which a defect is inspected by the macro observation using a partial illumination macro light source 10 and then subjected to the micro observation performed by the micro observation unit 9. In this case, the inspector places the substrate 3 at the right position on the holder 2 and adsorbed in the same manner as above. Then, the partial illumination macro light source 10 of the observation unit 6 is lighted on by the inspector to partially irradiate the surface of the substrate 3 mounted on the holder 2.

Subsequently, as shown in FIG. 3, the inspector operates an operation section (joystick, not shown) to move the observation unit 6 linearly along the guide rail of the observation unit supporting section 5 in the X-axis direction, and to move the observation unit supporting section 5 linearly along the guide rails 4, 4 in the Y-axis direction. While raster-scanning over the substrate 3 by the macro light 101, the inspector visually inspects scratches and spots over the entire surface of the substrate 3. In this case, the irradiation angle of the macro light 101 with the substrate 3 is adjusted so as to perform partial macro observation suitably.

In the partial macro observation using the partial illumination macro light source 10, when the inspector recognizes the defect in the substrate 3 under the illumination of the macro light 101, the observation unit 6 is moved along the X-axis and Y-axis by operating the operation section by the inspector so as to focus the spotlight of the reference light source 8 on the defect present in the substrate 3.

The position coordinates of the defect on the surface of the substrate 3 are determined by the controller 11 on the basis of the position coordinate data detected by the Y-scale 13 and X-scale 14. Subsequently, using the position coordination data and the previously stored data indicating the interval X0 between the optical axis of the reference light source 8 and the optical axis of the objective lens 91, the movements of the observation unit supporting section 5 and the observation unit 6 are controlled so as to permit the optical axis of the objective lens 91 to correspond with a specified defect present in the substrate 3.

Since the specified defect is brought into the center of the visual field of the objective lens 91 by the aforementioned operation, the micro observation of the defect can be made through the objective lens 91. At the same time, the defect obtained by the objective lens 91 is photographed by the TV camera 93. Therefore, the micro observation may be made on the TV monitor 12 by the inspector. In this case, the incident light can be used interchangeably with the transmission light depending upon types of the defects and substrates.

When the inspector instructs the macro observation again to the controller 11 through the input section 111, the defect is brought back within the illumination range of the macro light 101, so that an inspector can check the defect under the macro observation. If another defect is continuously observed, the same operation as mentioned above may be repeated. After the defect inspection is completed, the inspector gives a predetermined instruction to the controller 11 through the input section 111 to return the observation unit supporting section 5 to the initial position. The inspector removes the inspected substrate 3 from the holder 2, a new substrate 3 is mounted on and held by the holder 2.

In the case explained above, the macro observation is performed while the surface of the substrate 3 mounted on the holder 2 is partially illuminated with the partial illumination macro light source 10 and then the micro observation is performed when the defect is recognized in the substrate 3. In the case where only the macro observation is performed under illumination of the partial illumination macro light source 10, the operation is performed as follows. First, the inspector moves back the observation unit supporting section 5 to the initial position and mounts the substrate 3 on the holder 2. Then, the partial illumination macro light source 10 is lighted on to partially irradiating the surface of the substrate 3 on the holder 2 with the macro light 101 by the inspector. While the observation unit 6 is moved linearly in the X-axis direction along the guide rail of the observation unit supporting section 5 by operating the operation section and the observation unit supporting section 5 is further linearly moved in the Y-axis direction along the guide rails 4, 4, the substrate 3 is raster-scanned by use of the macro light 101. In this manner, the defect can be visually inspected over the entire surface of the substrate 3 by the inspector.

In this case, if the spotlight of the reference light source 8 is focused on each defect under the illumination of the macro light 101, the position coordinates of the defect are detected by detectors (not shown) respectively set at the X-scale and Y-scale. The detected position coordinates can be stored in the memory of the controller 11.

When the defect whose coordinate data is stored in the memory of the controller 11 is subjected to the micro observation by the micro observation unit 9, the operation is as follows. First, the inspector moves back the observation unit supporting section 5 to the initial position. Then, the inspector mounts the substrate 3 on the holder 2. The transmission linear light source 7 is lighted on, thereby irradiating the substrate linearly from the bottom of the holder 2 in the X-axis direction. Subsequently, the micro observation unit 9 is moved linearly under control of the controller 11 along the guide rail of the observation unit supporting section 5 in the X-axis direction. Consequently, the objective lens 91 is moved linearly in the X-direction along the transmission linear light source 7. Furthermore, the observation unit supporting section 5 is moved linearly in the Y-axis direction along the guide rails 4, 4. In this manner, a predetermined range of the substrate 3 can be observed microscopically via the objective lens 91. At the same time, the surface of the substrate 3 is photographed by the TV camera 93 and the image thereof is displayed on the TV monitor 12. Also in this case, the transmission light can be interchangeably used with the incident light depending upon the type of the substrate 3 and the defect.

According to the substrate inspecting apparatus of the present invention, the substrate 3 is raised at a predetermined angle by rotating the holder 2 having the substrate 3 held thereon, about the supporting shaft 15. By virtue of the operation, the substrate 3 is placed at a position close to an inspector's eye, so that the inspector can perform the macro inspection of the substrate 3 in an easy posture. In addition, the laser light source section 21, the beam splitter 214, the reflectors 215, 216, and the guide scales 19, 20 for use in detecting the position of the defect present in the substrate 3, are integrally provided on the rotatable (up and down) holder 2. It is therefore possible to detect the coordinates of the defect on the substrate 3 always in the same plane whenever the holder 2 is tilted at any angle. As a result, the coordinates of the defect can be detected highly accurately, and therefore a complicated process for amending the coordinate data depending upon the tilt angle is no longer required. The position coordinates (X, Y) of the defect can be determined only by detecting the positions of the reflectors 215 and 216 corresponding to the detect while manually moving them along the guide scales 19, 20 (which are provided along the side edges of the substrate 3). Therefore, the positional data of the defect can be easily obtained.

The observation unit 6 can be moved to any position on the substrate 3 by moving the observation unit supporting section 5 along one direction on the substrate 3 and moving the observation unit 6 in the direction perpendicular to the moving direction of the observation unit supporting section 5. As a result, the area of the holder 2 can be set at almost the same value as the substrate 3. As a result, miniaturization of the substrate inspecting apparatus can be realized. In addition, the area in which the substrate detection apparatus is placed, can be drastically reduced.

Figure 8:
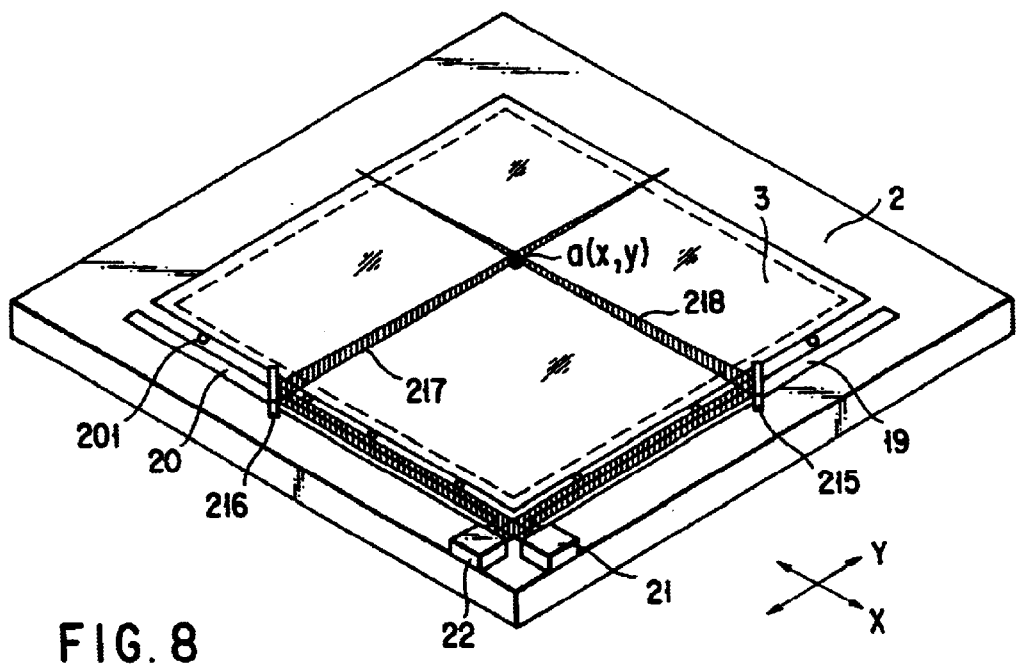
FIG. 8 is a view showing a structure of the position detector according to an embodiment of the present invention.

FIG. 8 is a view showing the structure of the position detector of the substrate inspecting apparatus according to Embodiment 2 of the present invention. In FIG. 8, like reference numerals are used to designate like structural elements corresponding to those in FIG. 7. The position detector is applied to the substrate inspecting apparatus shown in Embodiment 1. The position detector is constituted of two light source sections 21, 22 and reflectors (mirrors) 215, 216. Each of the light source sections 21, 22 has the laser light source 211 and the cylindrical lenses 212, 213 shown in FIG. 5.

The holder 2 has the guide scales 19, 20 formed in the Y-axis direction and the X-axis direction along a side of the substrate 3, as shown in FIG. 8. The guide scales 19, 20 play a role in detecting position coordinates of a defect present in the substrate 3. The guide scale 19 is equipped with the reflector (mirror) 215 in the Y-axis direction. The guide scale 20 is equipped with the reflector (mirror) 216 in the X-axis direction. The reflectors 215, 216 are movably provided along the guide scales 19, 20, respectively. The reflectors 215, 216 are set vertically at a right angle or an acute angle with the surface of the substrate 3. The holder 2 has the light source 21 at a position slightly apart from the right side of the guide scale 20 (the extension line of the guide scale 20). The light source section 22 is set at a position slightly ahead the guide scale 19 (the extension line of the guide scale 19).

The laser light emitted from the laser light source 211 of the light source section 21 transmits through the cylindrical lenses 212, 213 and finally emitted in the X-axis direction in the form of a planar laser virtually perpendicular to the surface of the substrate 3. The laser light is reflected by the reflector 216 in the perpendicular direction, namely, in the Y-axis direction, to become planar-form laser light 217 virtually perpendicular to the surface of the substrate 3. The laser light emitted from the laser light source 211 of the light source section 22 transmits through the cylindrical lenses 212, 213, and finally emitted in the Y-axis direction in the form of a planar laser light virtually perpendicular to the surface of the substrate 3. The laser light is reflected by the reflector 215 in the perpendicular direction, namely, in the X-axis direction, to become planer-form laser light 218 virtually perpendicular to the surface of the substrate 3.

In the same manner as in Embodiment 1, the inspector moves the reflector 215 along the guide scale 19 to permit the laser light 218 to correspond with the defect a formed in the surface of the substrate 3. Similarly, the inspector moves the reflector 216 along the guide scale 20 to permit the laser light 217 to correspond with the defect a. Thereafter, the inspector turns on the foot switch. The values of the guide scales 19, 20, that is, the moving amounts of the reflectors 215, 216 from the origins (the foremost position of the guide scale 19, the rightmost position of the guide scale 20 in FIG. 3) in the Y-axis and X-axis directions are determined by the detectors (not shown) of the guide scales 19, 20, as coordinates (X, Y) of the defect a. The detection results are output from the detectors to the controller 11.

According to the substrate inspecting apparatus according to Embodiment 2, the positional data of the defect can be easily obtained by moving the reflectors 215, 216 manually by the inspector.

Figure 9:
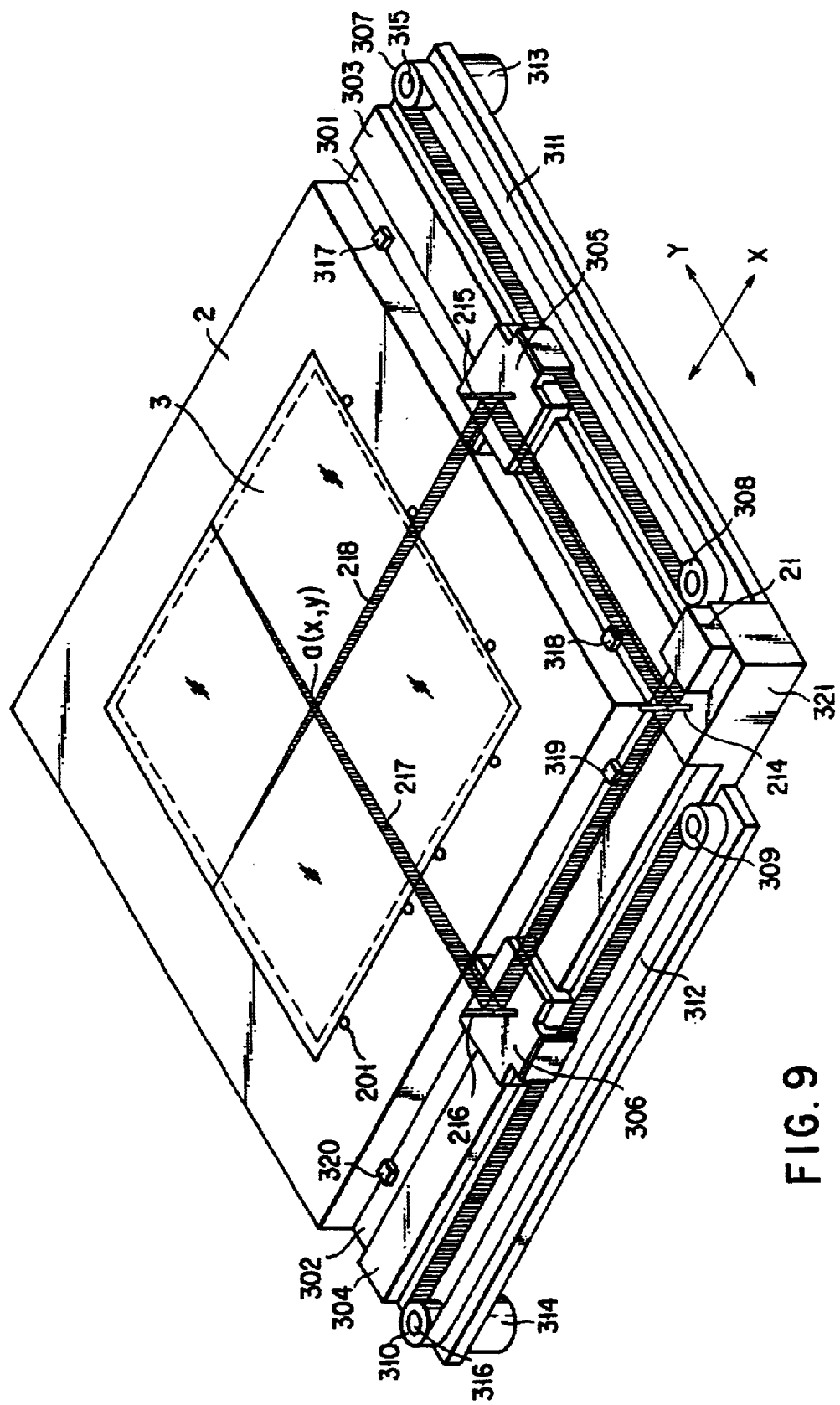
FIG. 9 is a view showing a structure of the position detector according to another embodiment of the present invention.

FIG. 9 is a view showing the structure of the position detector of the substrate inspecting apparatus according to Embodiment 3 of the present invention. In FIG. 9, like reference numerals are used to designate like structural elements corresponding to those in FIG. 7. The position detector can be applied to the substrate inspecting apparatus shown in Embodiment 1.

In FIG. 9, holding members 301, 302 are respectively provided on one of side surfaces of the holder 2 in the Y-axis direction and on one of side surfaces of the holder 2 in the X-axis direction, respectively. The surfaces of the holding members 301, 302 are lower than the surface of the holder 2, so that a step is formed between them. The holding members 301 and 302 are respectively equipped with guide rails 303, 304 along the Y-axis direction and the X-axis direction of the side edge of the holder 2. Furthermore, guide moving sections 305 and 306 are movably provided along the guide rails 303, 304 so as to cross over the guide rails 303, 304.

The holding members 301 and 302 have a pair of pulleys 307, 308, and a pair of pulleys 309, 310 supported by shafts and positioned respectively at both ends. A belt 311 and a belt 312 are respectively stretched between the pulley 307 and the pulley 308, and between the pulley 309 and pulley 310, in the form of a ring. The guide moving section 305 is fixed at a part of the belt 311. The guide moving section 306 is fixed at a part of the belt 312. To the pulleys 307, 310, respective rotation axis 315, 316 of the motors 313, 314 are inserted, respectively. A pair of optical sensors 317, 318 and a pair of optical sensors 319, 320 are respectively provided at one of side surfaces in the Y-axis direction and one of side surfaces in the X-axis direction of the holder 2, for detecting the presence of the guide moving sections 305, 306.

The guide moving section 305 is equipped with the reflector (mirror) 215 in the Y-axis direction. The guide moving section 306 is equipped with the reflector (mirror) 216 in the X-axis direction. These reflectors are vertically provided at a right angle or an acute angle with the surface of the substrate 3. A holding member 321 is provided at a point of intersection between the holding members 301 and 302. The holding member 321 is virtually as high as the holder 2. The beam splitter 214 is vertically provided on the holding member 321 at a point of intersection of the extension lines of the guide rails 303, 304, at a right angle or an acute angle with the surface of the substrate 3. The light source section 21 is set on the extension line of the guide rail 304 at a position slightly apart from the right side of the beam splitter 214. The light source section 21 is formed of the laser light source 211 and the cylindrical lenses 212, 213 as shown in FIG. 5.

The laser light emitted from the laser light source 211 of the light source section 21 transmits through the cylindrical lenses 212, 213, and finally emitted in the X-direction in the form of a planar laser light virtually perpendicular to the surface of the substrate 3. The laser light is split by the beam splitter 214 into two light beams in the X-direction and Y-direction. The laser light split in the X-axis direction is reflected by the reflector 216 and proceeds in the perpendicular direction, namely the Y-axis direction, in the form of a planar laser light 217 virtually perpendicular to the surface of the substrate 3. On the other hand, the laser light split in the Y-axis direction is reflected by the reflector 215 and proceeds in the perpendicular direction, namely, the X-axis, in the form of a planer laser light 218 virtually perpendicular to the surface of the substrate 3.

When the inspector operates the operation section (joystick) to drive the motor 313, the rotation shaft 315 moves in one direction, with the result that the belt 311 moves in said one direction along the Y-axis via the pulleys 307, 308. Alternatively, when the rotation shaft 315 is moved in the other (opposite) direction by moving the motor 313 by operating the operation section, the belt 311 moves in the other direction along the Y-axis via the pulleys 307, 308. Consequently, the reflector 215 on the guide moving section 305 is moved along the guide rail 303 to permit the laser light 218 to correspond with the defect a present in the substrate 3.

Furthermore, when the motor 314 is driven by operating the operation section by the inspector, the rotation shaft 316 is moved in one direction, with the result that the belt 312 moves in said one direction along the X-axis via the pulleys 310, 309. Alternatively, when the rotation shaft 316 is moved in the other direction (opposite direction) by driving the motor 314 under the control of the operation section, the belt 312 is moved in the other direction along the X-axis via the pulleys 310, 309. With this operation, the reflector 216 on the guide moving section 306 is moved along the guide rail 304 to permit the laser light 217 to correspond with the defect a present in the substrate 3.

Thereafter, the inspector turns on the foot switch. At this time, the values of guide scales (not shown) provided on the guide rails 303, 304, that is, moving amounts of the reflectors 215, 216 from the origins (positions of the sensors 318, 319) in the Y-axis direction and the X-axis direction, are detected by the detectors (not shown) of the guide scales as the coordinates (X, Y) of the defect a. The detection results are output from the detector to the controller 11.

Note that when the presence of the guide moving section 305 is detected by the sensor 317 or 318, the driving of the motor 313 is automatically stopped by the controller 11. This means that the guide moving section 305 can be moved back and forth on the guide rail 303 only between the position corresponding to the sensor 317 and the position corresponding to the sensor 318. Similarly, when the presence of the guide moving section 306 is detected by the sensor 319 or 320, the driving of the motor 314 is automatically stopped by the controller 11. This means that the guide moving section 306 is moved back and forth on the guide rail 304 only between the position corresponding to the sensor 319 and the position corresponding to the sensor 320.

According to the substrate inspecting apparatus of Embodiment 3 of the present invention, a single laser light source 21 is used and the guide moving sections 305, 306 equipped with the reflectors 215, 216 are electrically driven. It is therefore possible for an inspector to control the movements of the reflectors 215, 216 by operating the operation section manually. By virtue of this, in a specific case where a large substrate is inspected, the positional data of the defect present far away from the inspector can be readily determined. To move the guide moving sections 305, 306, a ball screw with a guide and a linear motor may be used.

The substrate inspecting apparatus of Embodiment 3 may be formed by setting two light source sections on the holder 2 instead of the beam splitter in the same manner as in Embodiment 2. The light from the light sources irradiates the reflectors 215, 216, respectively.

Figure 10:
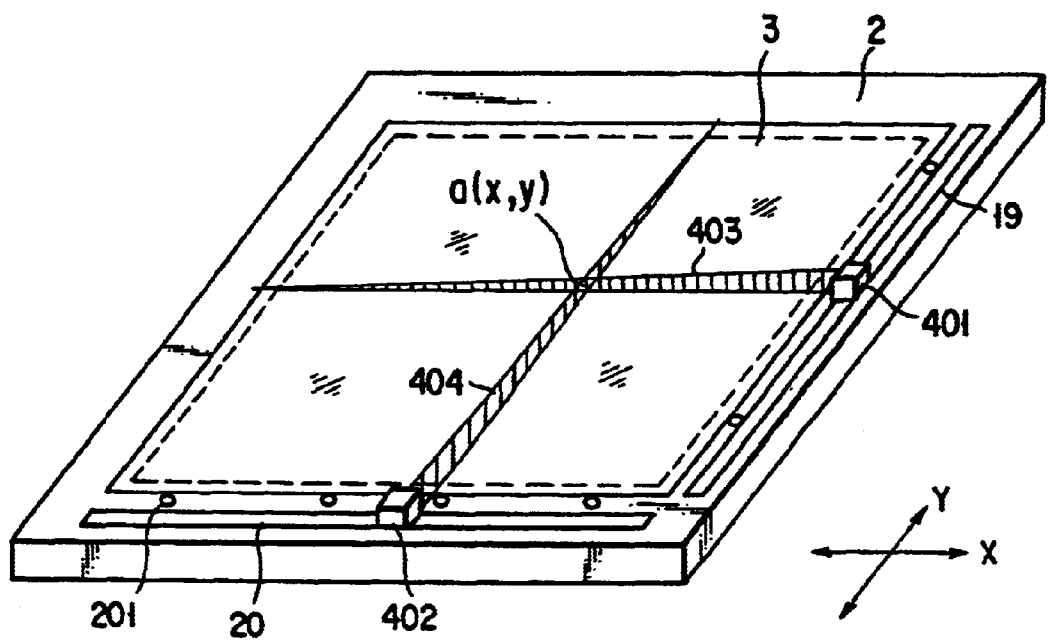
FIG. 10 is a view showing a structure of the position detector according to a further embodiment of the present invention.

FIG. 10 is a view showing a structure of the position detector of the substrate inspecting apparatus according to Embodiment 4 of the present invention. In FIG. 10, like reference numerals are used to designate like structural elements corresponding to those in FIG. 7. The position detector can be applied to the substrate inspecting apparatus shown in Embodiment 1. The position detector is constituted of two light source sections 401, 402. Each of the light source sections 401, 402 is constituted of the laser light source 211 and cylindrical lenses 212, 213 shown in FIG. 5.

As shown in FIG. 10, the holder 2 has the guide scales 19, 20 along the side edges of the substrate 3 in the Y-axis direction and X-axis direction, for detecting the position coordinates of the defect present in the substrate 3. The light source sections 401, 402 are movably provided on the guide scales 19, 20, respectively.

The laser light emitted from the laser light source 211 of the light source section 401 transmits through the cylindrical lenses 212, 213 and finally emitted in the X-axis direction in the form of a planar laser light 403 virtually perpendicular to the surface of the substrate 3. Similarly, the laser light emitted from the laser light source 211 of the light source section 402 transmits through the cylindrical lenses 212, 213 and finally emitted in the Y-axis direction in the form of a planar laser light 404 virtually perpendicular to the surface of the substrate 3.

In the same manner as in Embodiment 1, the inspector moves the light source section 401 along the guide scale 19 to permit the laser light 403 to correspond to the defect a in the surface of the substrate 3. Similarly the inspector moves the light source section 402 along the guide scale 20 to permit the laser light 404 to correspond with the defect a. Thereafter, the inspector turns on the foot switch. The values of the guide scales 19, 20, that is, moving amounts of the light source sections 401, 402 from the origins (the foremost position of the guide scale 19, the rightmost position of the guide scale 20 in FIG. 10) in the Y-axis and X-axis directions are determined by the detectors (not shown) of the guide scales 19, 20, as coordinates (X, Y) of the defect a. The detection results are output from the detector to the controller 11.

According to the substrate inspecting apparatus of Embodiment 4 of the present invention, two laser light source sections 401, 402 are provided on the guide scales 19, 20. Different from the constitutions of Embodiments 1 and 2, the beam splitter and reflectors are not used. The inspector can easily determine the positional data of the defect only by moving the light sources 401, 402, manually. Note that the substrate inspecting apparatus of Embodiment 4 may be formed in the same manner as in Embodiment 3. That is, the laser light sources 401, 402 are provided on the guide moving sections 305, 306 and the laser light sources 401, 402 may be electrically moved along the guide scales 19, 20.

Figure 11:
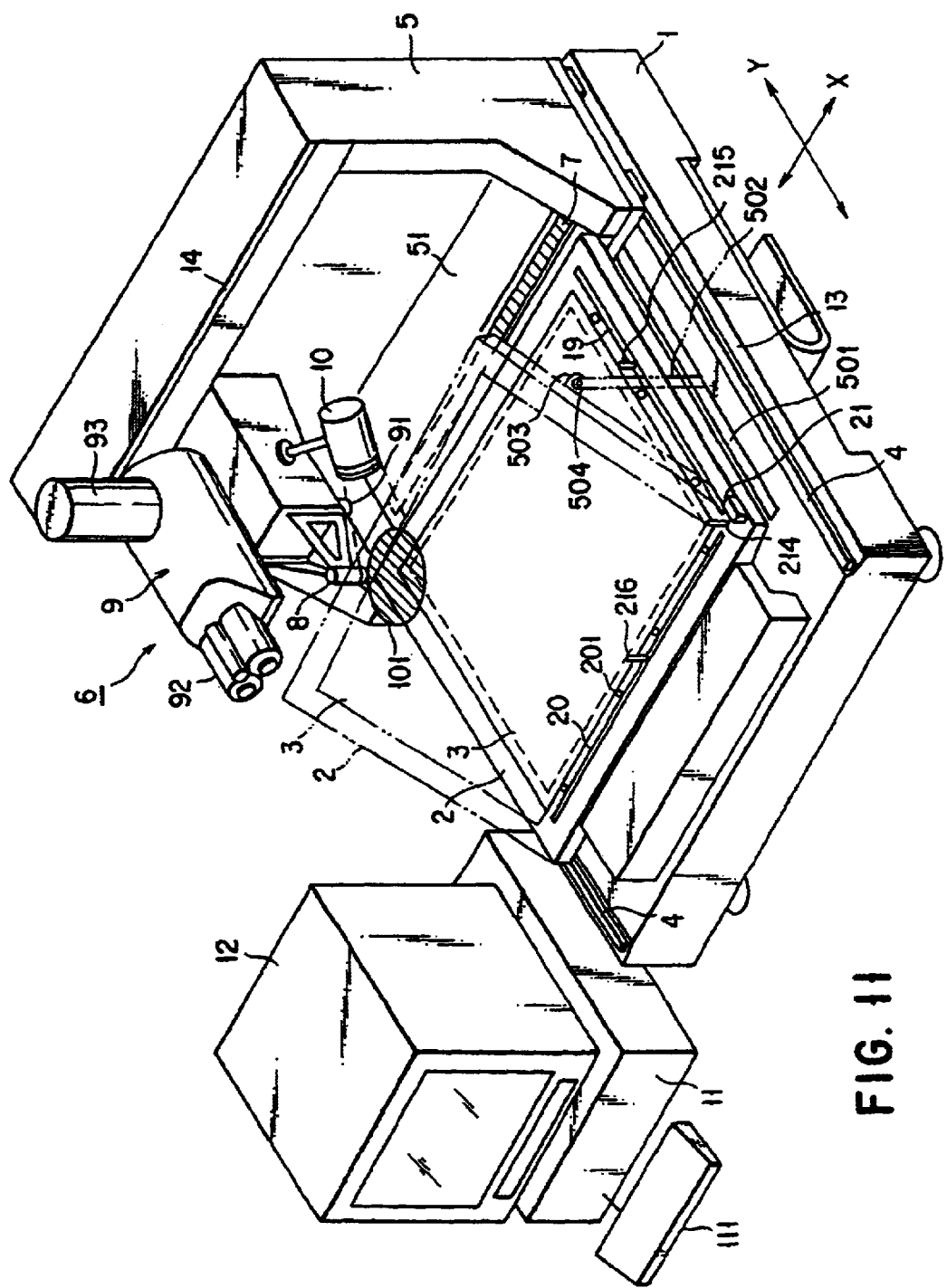
FIG. 11 is a perspective view of the substrate inspecting apparatus according to an embodiment of the present invention.
Figure 12:
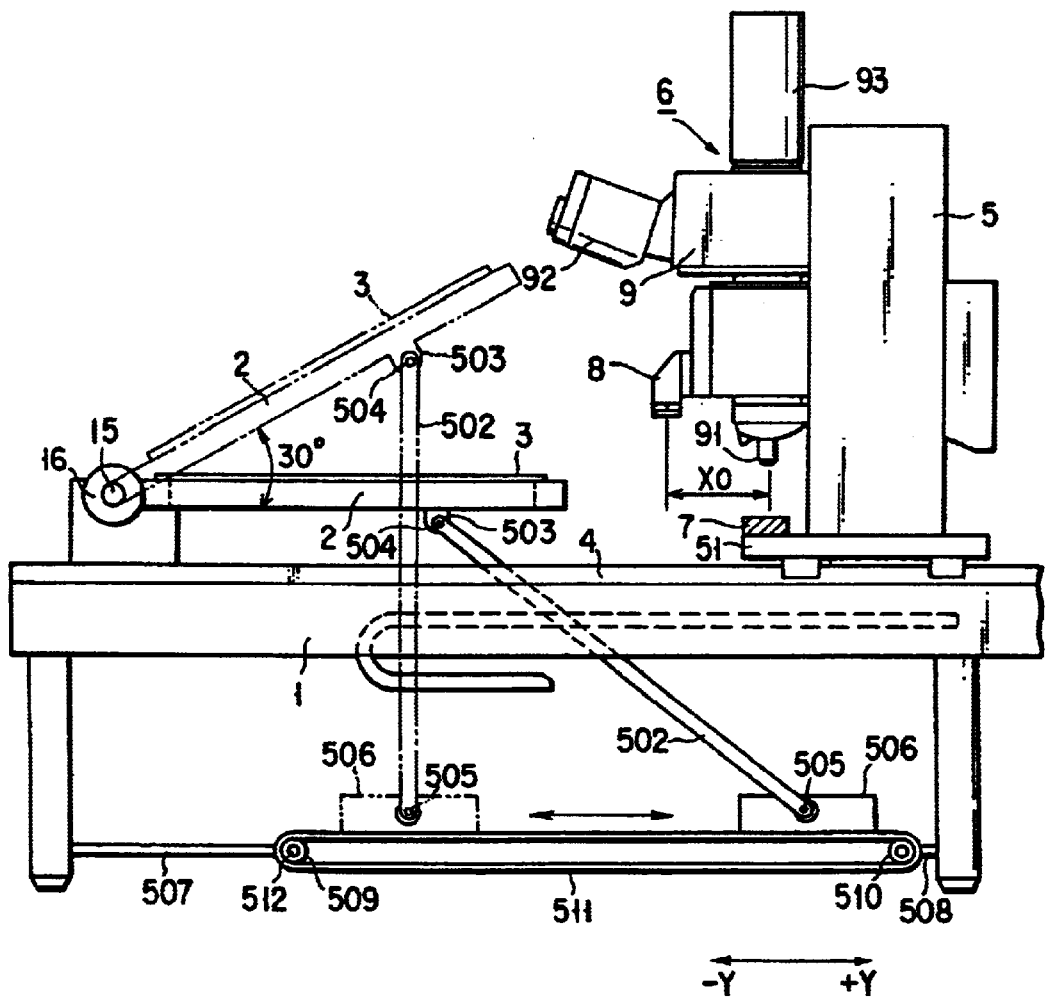
FIG. 12 is a side view of the substrate inspecting apparatus according to the embodiment of the present invention.

FIGS. 11 and 12 show the structure of a substrate inspecting apparatus according to Embodiment 5 of the present invention. FIG. 11 is a perspective view thereof and FIG. 12 is a side view thereof. In FIGS. 11 and 12, like reference numerals are used to designate like structural elements corresponding to those in FIGS. 1 and 2, and any further explanation is omitted for brevity's sake. In the substrate inspecting apparatus shown in FIGS. 1 and 2, the rotation driving force of the motor 18 is transmitted from the rotation shaft 181 to the pulley 16 by way of the belt 17, whereby the holder 2 is lifted from the horizontal posture up to a predetermined angle around the supporting axis. In the substrate inspecting apparatus according to Embodiment 5, the holder 2 is lifted up in a swinging manner by a link mechanism to a predetermined angle and allow to stand in an inclined posture.

As shown in FIG. 11, on the main apparatus body 1, a long and narrow hole 501 is formed along the side of the holder 2 arranged horizontally. Through the hole 501, a connecting member 502 is inserted. On the side surface of the holder 2, a hook 503 is formed so as to cross at a right angle with the surface of the holder 2 on which the substrate 3 is mounted. An end of the connecting member 502 is rotatably connected to the hook 503 via a rotation shaft 504. The other end of the connecting member 502 is rotatably connected to a moving piece 506 via the rotation shaft 505 below the main apparatus body 1, as shown in FIG. 12.

Furthermore, as shown in FIG. 12, pulleys 509, 510 are provided respectively at ends of holding members 507, 508 while being supported by a shaft. The belt 511 is stretched between the pulleys 509 and 510 in a ring form. The moving piece 506 is fixed onto a part of the belt 511. The rotation shaft 512 of a motor (not shown) is inserted in the pulley 509.

The inspector operates a holder operation section (not shown) to drive the motor. At this point, when the rotation shaft 512 is rotated counterclockwise, the belt 511 is moved in the "−Y" direction via the pulleys 509, 510. Alternatively, when the rotation shaft 512 is rotated clockwise by driving the motor, the belt 511 is moved in the "+Y" direction via the pulleys 509, 510. With this movement, the moving piece 506 fixed on the belt 511 is moved in the −Y direction and +Y direction (forward and backward to the holder 2).

As shown in FIG. 12, when the moving piece 506 moves in the −Y direction while maintaining the holder 2 horizontally, the end of the connecting member 502 connected to the moving piece 506 rotates clockwise by the rotation shaft 505. As a result, the connecting member 502 is gradually lifted up from the inclined posture. In accordance with this movement, the end of the connecting member 502 pushes up the holder 2 via the hook 503 while rotating around the rotation shaft 504, with the result that the holder 2 is rotated at an angle of about 30° around the supporting shaft 15 and lifted up to a position indicated by a two dot-and-dash line from the horizontal posture, allowing the holder 2 to stand up in an inclined posture. Thereafter, the inspector terminates the movement of the motor to stop the holder 2. Subsequently, the macro observation is performed.

After completion of the macro observation of the entire substrate 3, the inspector operates the holder operation section again to drive the motor. When the rotation axis 512 is rotated clockwise, the moving piece 506 is moved in the +Y direction via the pulleys 509, 510 and the belt 511. Upon the movement of the moving piece 506 in the +Y direction, the end of the connection member 502 connected to the moving piece 506 is rotated counterclockwise by the rotation axis 505. As a result, the connecting member 502 is gradually inclined from the stand-up posture. With this movement, the end of the connecting member 502 brings down the holder 2 via the hook 503 while rotating the end of the connecting member 502 around the rotation shaft 504. Consequently, the holder 2 returns in a horizontal posture initially taken. In this state, the micro observation is performed by the inspector. The moving piece 506 may be moved back and forth by a well known ball-screw or a linear motor in place of the belt.

As described in the above, it is possible to lift up the holder 2 up to an angle of about 30° by using the link mechanism because of the swing movement of the holder 2. In addition, since the holder 2 is supported by the connecting member 502 when lifted up, the macro observation can be performed while setting the holder 2 in a more stable posture.

Figure 13:
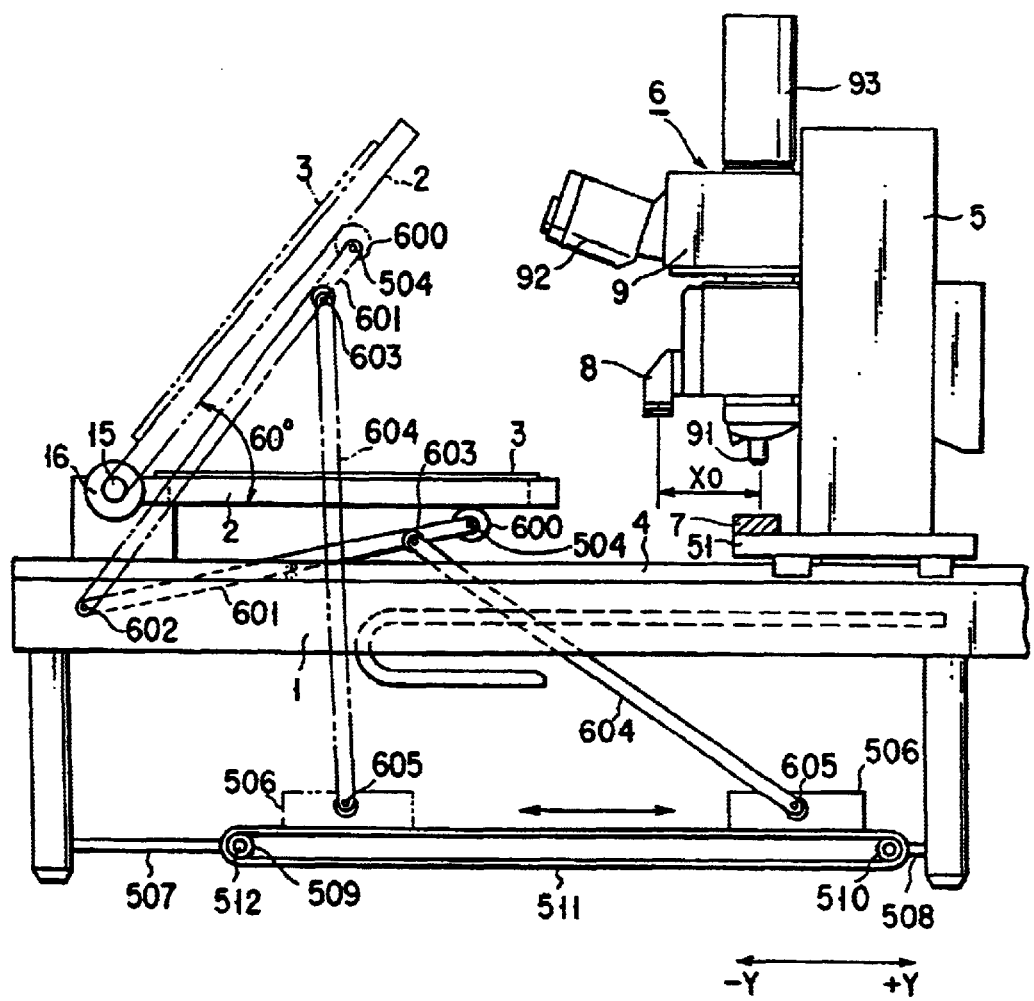
FIG. 13 is a side view of the substrate inspecting apparatus according to another embodiment of the present invention.

FIG. 13 is a side view of the structure of a substrate inspecting apparatus according to Embodiment 6 of the present invention. In FIG. 13, like reference numerals are used to designate like structural elements corresponding to those in FIG. 12, and any further explanation is omitted for brevity's sake. In Embodiment 5, the link mechanism is constituted by using a single connecting member, whereas the link mechanism is constituted by using two connecting members in Embodiment 6.

As shown in FIG. 13, the proximal end of a first connecting member 601 is rotatably connected by a rotation shaft 602 to the main apparatus body 1 while being supported by the shaft. To the free end of the first connecting member 601, a roller 600 moving on the rear surface of the holder 2 is rotatably connected while being supported by the shaft. To the position near the free end of the first connecting member 601, an end of a second connecting member 604 is rotatably connected via a rotation axis 603. The other end of the second connecting member 604 is rotatably connected to the moving piece 506 via a rotation axis 605 below the main apparatus body 1.

As shown in FIG. 13, when the moving piece 506 moves in the −Y direction while maintaining the holder 2 in the horizontal posture, the other end of the second connecting member 604 connected to the moving piece 506 rotates clockwise by the rotation axis 605. As a result, the second connecting member 604 is gradually lifted up from the inclined posture. With this movement, the end of the second connecting member 604 lifts up the first connecting member 601 while rotating around the rotation axis 603. Further, with this movement, the roller 600 of the first connecting member 601 rotatably moves on the rear surface of the holder 2 and pushes up the holder 2. As a result, the holder 2 is lifted up at an angle of about 60° around the supporting shaft 15 to a position indicated by a two dot-and-dash line from the horizontal posture, allowing the holder 2 to stand in an inclined posture. After the holder 2 is allowed to stand in the inclined posture, the inspector terminates the movement of the motor to stop the holder 2. Thereafter, the macro observation is performed.

When the moving piece 506 moves in the +Y direction, from this state, the other end of the second connection member 604 connected to the moving piece 506 is rotated counterclockwise by the rotation axis 605. As a result, the second connecting member 604 is gradually inclined from the stand-up posture. Accordingly, the end of the second connecting member 604 brings down the first connecting member 601 while rotating around the rotation shaft 603. With this movement, the holder 2 is brought down following the movement of the roller 600 of the first connecting member 601. Consequently, the holder 2 returns in a horizontal posture initially taken. In this state, the micro observation is performed by the inspector.

As described above, the link mechanism is constituted by using two connecting members in order to swing the holder 2. With the structure, the holder 2 can be lift up to about an angle of 60° and allowed to stand in an inclined posture. If the holder 2 is lifted up to about 60° by means of one connecting member in Embodiment 5, very long connecting member is required. As a result, a broad space is required to set the apparatus. However, in Embodiment 6, since double link mechanism is constituted by using two connecting members, the holder 2 can be swung to be lifted up to about 60°. In addition, since the link mechanism is formed by employing two short connecting members, the space occupied by the apparatus can be saved.

The link mechanisms shown in Embodiments 5 and 6 may be applied to the substrate inspecting apparatuses shown in Embodiments 1 to 4.

According to the present invention, the following functions are obtained.

According to the substrate inspecting apparatus of the present invention, the substrate holding member can be raised at a predetermined angle while holding the substrate. It is therefore possible to perform the macro observation of the surface of the substrate from a position close to the eye of an inspector. Hence, the defect can be inspected highly accurately. In addition, since the position coordinates of the defect present in the substrate are determined by the position detector, the micro observation system is controlled on the basis of the coordinates so as to correspond to the defect present in the substrate. As a result, the micro observation can be made smoothly and continuously following the macro observation, increasing the efficiency of the defect inspection by the macro observation and the micro observation.

According to the substrate inspecting apparatus of the present invention, it is possible to determine the position coordinates of the defect easily only by detecting the position of the position detector corresponding to the defect while moving the position detector along the guide scale provided along the side edge of the substrate.

According to the substrate inspecting apparatus of the present invention, the observation unit can be moved in any position on the substrate only by moving the observation unit supporting section on the substrate in one direction and moving the observation unit in the direction perpendicular to the moving direction of the observation unit supporting section. It is therefore possible to form the substrate holding member in virtually the same size as the substrate. Hence, miniaturization of the apparatus is attained and the setting area of the apparatus can be drastically reduced.

Furthermore, in the present substrate inspecting apparatus, the electrical wiring for providing the light source section on the guide scale can be made simply by moving the reflector. In addition, the space required for the wiring can be reduced. Hence the miniaturization of the apparatus is attained. Since the apparatus can be constituted by using only one light source, the apparatus can be formed inexpensively.

According to the substrate inspecting apparatus of the present invention, the movement of the reflector can be controlled by a predetermined manual operation the inspector performed at a proximal side of the apparatus. Therefore, in a specific case where a large substrate is inspected, the positional data of the defect can be easily obtained even if the defect is present far away from the inspector.

According to the substrate inspecting apparatus of the present invention, a connecting function is used to swing the substrate holding member. It is therefore possible to lift up the substrate holding member up to an angle of about 30°. Since the substrate holding member is supported by the connecting function when lifted up, the macro observation is performed while the substrate holding member is placed in a stable state.

According to the substrate inspecting apparatus of the present invention, the connecting function is constituted of a plurality of connecting members. It is therefore possible to lift up the substrate holding member in a swinging manner to an angle of about 60°. Furthermore, the link mechanism is constituted by using a plurality of short connecting members. It is therefore possible to save the space for setting the apparatus.

To be more specifically, the present invention makes it possible not only to reduce the size of the substrate inspecting apparatus but also to increase the accuracy and efficiency in inspection of the substrate inspecting apparatus.

Note that the present invention is not limited to the aforementioned Embodiments and may be modified within the scope of the present invention.

Additional advantages and modifications will readily occurs to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An inspecting apparatus comprising:
   a main body;
   a substrate holder which is arranged horizontally above an upper surface of the main body and which holds a substrate to be inspected;

a pair of guide rails arranged on the main body along respective sides of the substrate holder in an opposing manner;

an observation unit supporting section comprising a pair of support columns respectively traveling along the guide rails and a horizontal arm section connecting the support columns;

a micro inspection unit which is movable along the horizontal arm section in a direction perpendicular to the guide rails, and which includes an objective lens for microscopically observing a surface of the substrate to be inspected;

a storage section which stores position coordinates of at least one defect on the substrate to be inspected; and a control section which controls movement of the observation unit supporting section and the micro inspection unit so that an observation optical axis of the objective lens of the micro inspection unit is adjusted to the defect on the substrate to be inspected based on the position coordinates of the defect read from the storage section.

2. The inspecting apparatus according to claim 1, wherein the guide rails have extensions situated behind a rear end of the substrate holder and the control section controls movement of the observation unit supporting section so that the observation unit supporting section is retreated in the extensions of the guide rails, when the substrate to be inspected is supplied to the substrate holder.

3. The inspecting apparatus according to claim 1, wherein the observation unit supporting section is integrally provided with a transmission light source arranged under the substrate holder so as to face a track of movement of the micro inspection unit.

4. The inspecting apparatus according to claim 3, wherein the transmission light source comprises a linear light source which linearly illuminates the substrate to be inspected.

5. The inspecting apparatus according to claim 3, wherein the transmission light source includes:

a light source which supplies illumination light;

a glass rod which transmits the illumination light therethrough; and white stripes applied on a rear portion of the glass rod to disperse the illumination light transmitted through the glass rod toward the objective lens of the micro inspection unit.

6. The inspecting apparatus according to claim 1, wherein:

the micro inspection unit includes a TV camera which picks up an image of the surface of the substrate to be inspected taken through the objective lens; and the control section displays the image picked up by the TV camera on a TV monitor.

7. The inspecting apparatus according to claim 1, wherein the micro inspection unit includes an ocular lens for observing an image of the surface of the substrate to be inspected taken through the objective lens.

8. The inspecting apparatus according to claim 1, wherein:

the micro inspection unit includes a reference light source which is separated by a predetermined distance from the observation optical axis of the objective lens and which projects a spot light to designate a position of the defect on the substrate to be inspected;

the observation unit supporting section and the micro inspection unit include coordinate scales which detect coordinates of positions thereof, respectively;

the storage section stores coordinate data from the respective coordinate scales of the observation unit supporting section and the micro inspection unit; and the control section obtains the position coordinates of the defect from the coordinate data of the respective coordinate scales read from the storage section, and controls movement of the observation unit supporting section and the micro inspection unit so that the observation optical axis of the objective lens of the micro inspection unit is adjusted to the defect on the substrate to be inspected based on the coordinate data and the predetermined distance.

9. The inspecting apparatus according to claim 8, further comprising a partial illumination macro light source which is movable along the horizontal arm section in the direction perpendicular to the guide rails, and which partially and macroscopically illuminates the surface of the substrate to be inspected; and wherein the control section controls movement of the observation unit supporting section and the partial illumination macro light source in X and Y directions and causes the partial illumination macro light source to perform raster scanning of the surface of the substrate to be inspected.

* * * * *

UNITED STATES PATENT AND TRADEMARK OFFICE
Certificate

Patent No. 6,707,546 B2                                                    Patented: March 16, 2004

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Hiroyuki Okahira, Ina (JP); Yuzo Nakamura, Ina (JP); and Terumasa Morita, Hachioji (JP)

Signed and Sealed this Third Day of August 2010.

*Gregory J. Toatley, Jr.*
*Supervisory Patent Examiner*
*Art Unit 2877*
*Technology Center 2800*